United States Patent [19]

Casciani

[11] Patent Number: 4,992,211
[45] Date of Patent: Feb. 12, 1991

[54] ALKYLENE OXIDE-CONTAINING AMPHOTERIC SURFACTANTS

[75] Inventor: Robert V. Casciani, Charlotte, N.C.

[73] Assignee: Sandoz Ltd., Basel, Switzerland

[21] Appl. No.: 439,723

[22] Filed: Nov. 21, 1989

Related U.S. Application Data

[63] Continuation-in-part of Ser. No. 278,070, Nov. 30, 1988.

[51] Int. Cl.$^5$ .................... C11D 7/32; A01K 7/06; C07C 67/02; C07C 225/00
[52] U.S. Cl. .................... 252/541; 252/546; 252/DIG. 7; 252/DIG. 13; 424/70; 560/251; 564/292; 564/294
[58] Field of Search ......... 252/542, 546, 564, DIG. 7, 252/541, DIG. 13; 562/564; 424/70; 560/251; 564/292, 294

[56] References Cited

U.S. PATENT DOCUMENTS

| | | | |
|---|---|---|---|
| 3,912,662 | 10/1975 | Martinsson et al. | 252/546 |
| 3,928,251 | 12/1975 | Bolich et al. | 252/DIG. 7 |
| 3,950,417 | 4/1976 | Verdicchio et al. | 252/DIG. 7 |
| 4,486,328 | 12/1984 | Knott et al. | 252/546 |
| 4,511,513 | 4/1985 | Guth et al. | 562/564 |
| 4,555,360 | 11/1985 | Bisset et al. | 252/DIG. 7 |
| 4,681,704 | 7/1987 | Bernardino et al. | 252/546 |
| 4,830,782 | 5/1989 | Broze et al. | 252/546 |
| 4,885,112 | 12/1989 | Sotoya et al. | 252/546 |

FOREIGN PATENT DOCUMENTS 89458  5/1985  Japan .

Primary Examiner—Paul Lieberman
Assistant Examiner—James M. Silbermann
Attorney, Agent, or Firm—Gerald D. Sharkin; Robert S. Honor; Joseph J. Borovian

[57] ABSTRACT

The invention relates to novel alkylene oxide-containing amphoteric compounds and to their use as surface active agents. The novel amphoteric compounds are especially useful in the cosmetics and toiletries areas, e.g., as surfactants in shampoo compositions.

13 Claims, 1 Drawing Sheet

VISCOSITY RESPONSE TO NACL

+ C2M (60rpm)

• EX. 3 (60rpm)

ALKYLENE OXIDE-CONTAINING AMPHOTERIC SURFACTANTS

This is a continuation-in-part of U.S. patent application Ser. No. 07/278,070, filed Nov. 30, 1988, now abandoned.

This invention relates to a new class of surface active agents. More particularly, it relates to certain alkylene oxide-containing amphoteric compounds and to their use as surface active agents in a wide variety of consumer product areas. The alkylene oxide-containing amphoteric compounds are especially useful in the cosmetics and toiletries areas, e.g., as surfactants in shampoo compositions.

To an outsider looking in, the search for a surfactant for use in shampoo compositions is relatively easy since new surfactants appear in the literature regularly. However, and as is well known by those skilled in the art, the formulation of shampoo compositions for human hair is a highly specialized field involving many considerations, viz., cleaning ability, foaming action, mildness, etc. More often than not, a surfactant is chosen primarily on the basis of its cleaning ability at the expense of serious compromises in overall product behavior.

In the past, soap-based shampoo compositions were employed. Unfortunately, they suffered from the disadvantage of dulling the hair due to the precipitation thereon of lime and magnesium soap or the like, especially in hard water. In addition, such precipitates considerably reduced the foaming action of the shampoo compositions. Faced with the problems exhibited by soap-based shampoo compositions, those skilled in the art attempted to overcome these drawbacks by the substitution, in part, of synthetic organic detergents, e.g., sulfates and sulfonates, for the soap. However, shampoo compositions based on mixtures of synthetic detergents and soaps appear to be rather deficient and offer little in value to the demanding consumer. For instance, when such mixtures are brought into contact with calcium ions in water, the lime soaps which necessarily form must be dispersed by the synthetic detergent. Consequently, not only is a part of the soap lost by binding to calcium, when such ions are present, but also part of the synthetic detergent is consumed as a dispersing agent for the lime soap formed and thereby loses a certain degree of its cleaning action. In this connection, it should be kept in mind that in the washing of human hair, even a professional hairdresser normally uses tap water.

More recently, shampoo compositions have surfaced which contain, as the essential cleaning component, a synthetic detergent or a mixture thereof, exclusively. However, although such shampoo compositions exhibit acceptable cleaning and foaming properties, the presence of the synthetic detergent or mixture thereof appears to enhance the irritation potential of the shampoo compositions, thereby making them unacceptable from a mildness standpoint. In an effort to overcome the enhanced irritation potential of synthetic detergent-based shampoo compositions, the skilled artisan has modified the synthetic detergent component, e.g., a higher alkyl ether sulfate of the formula $$R(OCH_2CH_2)_m-OSO_3M$$

where R is $C_{10}$–$C_{15}$alkyl, m is an integer 1 to 3 and M is a cation, by increasing the level of ethylene oxide. However, such a modification, although somewhat ameliorating the irritation potential of the above-identified alkyl ether sulfates, adversely affects the foaming properties of the shampoo compositions.

Accordingly, it is an object of the present invention to provide a new class of surface active agents. It is another object of the present invention to provide a new class of surface active agents which are useful in a wide variety of consumer product areas. It is still another object of the present invention to provide certain alkylene oxide-containing amphoteric surfactants which are especially useful in the cosmetics and toiletries areas. It is yet still another object of the present invention to provide certain alkylene oxide-containing amphoteric compounds which may be employed as the essential surfactant in shampoo compositions, wherein said compositions exhibit exceptional cleaning and foaming properties. A further object of the present invention is to provide certain alkylene oxide-containing amphoteric compounds exhibiting a high degree of salt tolerance, thereby enabling high active levels of said compounds to be achieved at lower viscosities.

Figure 1:
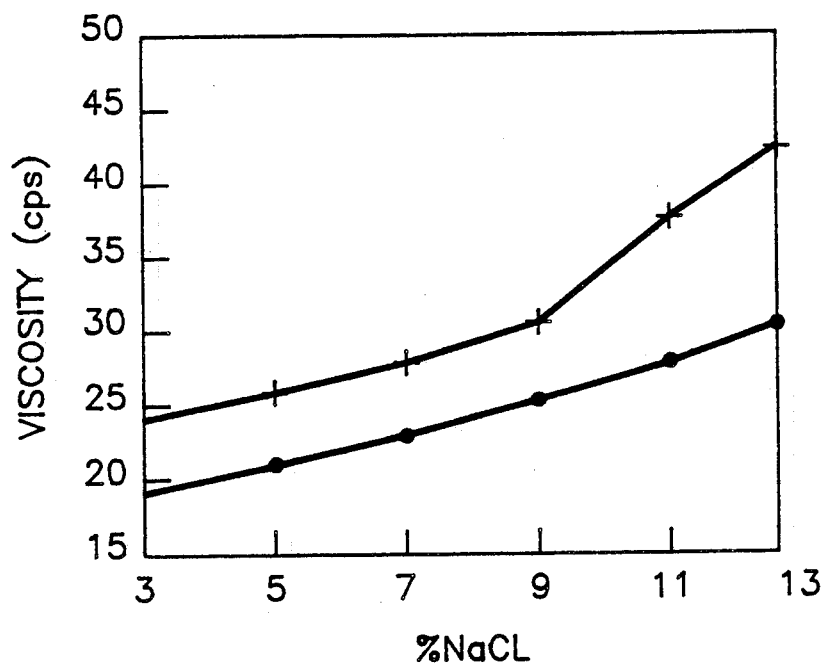
FIG. 1 shows the viscosity of the title compound compared to that of Miranol C2M measured with a Brookfield LVT viscometer at 60 rpm while varying the salt concentration.

The attainment of the above objects is made possible by certain alkylene oxide-containing amphoteric compounds of formula I:

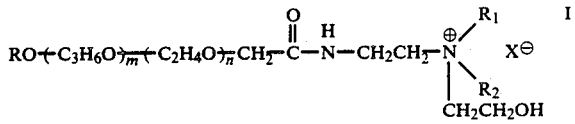

where
- R is $C_6$–$C_{22}$ straight or branched chain alkyl or a group $R^1$—$C_6H_4$, where R' is $C_6$–$C_{16}$ straight or branched chain alkyl;
- $R_1$ is —$CH_2COOM$, where M is hydrogen or a cation selected from alkali metal, alkaline earth metal, ammonium, mono-, di- and tri-$C_2$–$C_4$alkanolammonium and mono-, di-, tri- and tetra- $C_1$–$C_4$alkylammonium;
- $R_2$ is hydrogen or —$CH_2COOM$, where M is as defined above;
- m is 0 or an integer 1 to 10;
- n is an integer 2 to 15; and
- $X^\ominus$ is an anion, or a mixture of said compounds.

With respect to the "ammonium salt" portion of formula I above, i.e.,

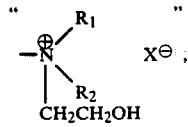

the structural formula depicts one possible ionic form. However, it is clearly evident that, in aqueous solution, solvation of the ions would lead to an equilibrium condition which would allow the corresponding zwitterionic form to exist with the solvated $M_s^\oplus$ and $X_s^\ominus$ ions according to the reaction scheme below:

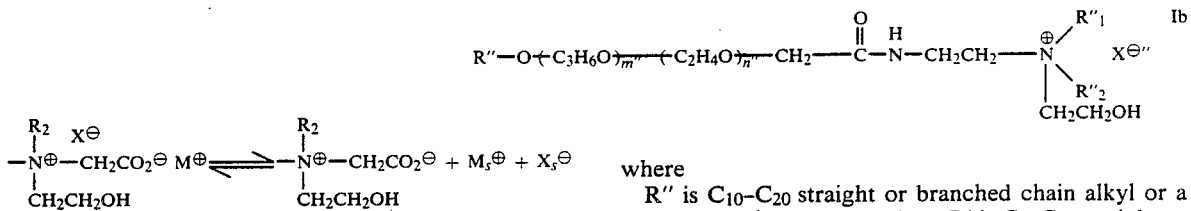

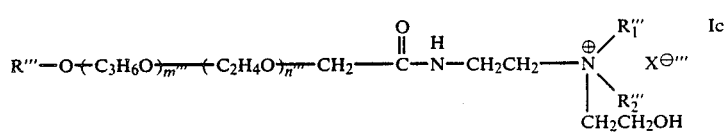

When R is straight or branched chain alkyl, said alkyl group preferably contains 8 to 20 carbon atoms, more preferably 10 to 20 carbon atoms, and even more preferably 12 to 18 carbon atoms.

When R is a group $R'—C_6H_5—$, the R' portion preferably contains 6 to 14 carbon atoms, more preferably 8 to 12 carbon atoms, and even more preferably 9 to 12 carbon atoms.

The hydroxy group of any $C_2-C_4$ hydroxyalkyl group in M is on other than the α-carbon atom. When M has more than one $C_2-C_4$ hydroxyalkyl or $C_1-C_4$ alkyl group, they may be the same of different but are preferably the same. Preferably, M does not contain more than two tertiary butyl groups. The preferred alkali metals as A are lithium, sodium and potassium and the preferred alkaline earth metals are magnesium, calcium, barium and strontium.

The variable m is preferably 0 or an integer 1 to 5, more preferably 0 or an integer 1 to 3, and even more preferably 0 or an integer 1 or 2.

The variable n is preferably an integer 2 to 12, more preferably an integer 3 to 10, and even more preferably an integer 4 to 9.

The anion $X^\ominus$ is preferably a halide, more preferably chloride or bromide, and even more preferably chloride.

The preferred compounds of formula I are those of formula Ia:

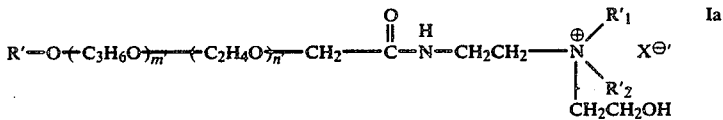

where
R' is $C_8-C_{20}$ straight or branched chain alkyl or a group $R^1—C_6H_4—$, where R' is $C_6-C_{14}$ straight or branched chain alkyl;
$R_1'$ is $—CH_2COOM'$, where M' is hydrogen or a cation selected from alkali metal, alkaline earth metal and ammonium;
$R_2'$ is hydrogen or $—CH_2COOM'$, where M' is as defined above;
m' is 0 or an integer 1 to 5;
n' is an integer 2 to 12; and
$X^{\ominus'}$ is halide, or a mixture of said compounds.

The more preferred compounds of formula I are those of formula Ib:

where
R'' is $C_{10}-C_{20}$ straight or branched chain alkyl or a group $R^1—C_6H_4—$, where R' is $C_8-C_{12}$ straight or branched chain alkyl;
$R_1''$ is $—CH_2COOM'$, where M' is hydrogen or a cation selected from alkali metal and ammonium;
$R_2''$ is hydrogen or $—CH_2COOM'$, where M' is as defined above;
m'' is 0 or an integer 1 to 3;
n'' is an integer 3 to 10; and
$X^{\ominus''}$ is chloride or bromide, or a mixture of said compounds.

The even more preferred compounds of formula I are those of formula Ic:

where
R''' is $C_{12}-C_{18}$ straight or branched chain alkyl or a group $R^1—C_6H_4—$, where R' is $C_9-C_{12}$ straight or branched chain alkyl;
$R_1'''$ is $—CH_2COOM'$, where M' is hydrogen or a cation selected from sodium, potassium and ammonium;
$R_2'''$ is hydrogen or $—CH_2COOM'$, where M' is as defined above;
m''' is 0, or an integer 1 or 2;
n''' is an integer 4 to 9; and
$X^{\ominus'''}$ is chloride, or a mixture of said compounds.

Suitable precursors of the alkylene oxide-containing amphoteric compounds of this invention are straight or branched chain primary alcohols having from 6 to 22 carbon atoms. Typical examples of alcohols having a straight chain configuration are n-hexyl, n-heptyl, n-octyl, n-nonyl, n-decyl, n-undecyl, n-dodecyl, n-tridecyl, n-tetradecyl, etc., whereas isodecyl and isostearyl are exemplary of alcohols having a branched chain configuration. A mixture of alcohols may be used and this is generally true when using commercial alcohols which are often available as a blend of several alcohols Specific examples are a mixture of $C_{12}-C_{15}$ straight chain alcohols available commercially from Union Carbide; a mixture of $C_{12}-C_{15}$ predominantly straight chain alcohols containing approximately 20% branching available commercially from Shell Chemical Co.; and a mixture of alcohols, at least 70 mol % of which is branched 1-decanols available commercially from Exxon Chemical Co. When employing a mixture of alcohols, the number of carbon atoms in the alcohol is referred to as an average number and such number can be determined by vapor phase chromatography and the hydroxyl number.

Other suitable precursors of the alkylene oxide-containing amphoteric compounds of this invention are straight or branched chain alkylphenols having from 6 to 16 carbon atoms in the alkyl portion thereof. Typical examples of alkylphenols having a straight chain configuration are n-hexaphenol, n-decylphenol, n-dodecylphenol, n-tetradecylphenol, etc., whereas i-octylphenol and branched chain nonylphenol are exemplary of alkylphenols having a branched chain configuration.

The compounds of formula I are produced by more or less conventional methods. Thus, the alkylene oxide-containing amphoteric compounds of this invention may be prepared by carboxyalkylating the adduct resulting from the propoxylation and/or ethoxylation of a straight or branched chain primary alcohol having from 6 to 22 carbon atoms or a straight or branched chain alkylphenol having from 6 to 16 carbon atoms in the alkyl portion thereof, reacting the carboxyalkylated adduct resulting therefrom with an appropriate amine via a condensation reaction and then carboxyalkylating the amidoamine intermediate resulting therefrom to realize a compound of formula I where $R_2$ is hydrogen. Further carboxyalkylation of said compound results in a compound of formula I where $R_2$ is —$CH_2COOM$.

More particularly, a catalytic amount, e.g., from about 0.2% to 1%, preferably 0.3% to 0.75%, by weight of the total amount of reactants, including the respective alkylene oxides, of an alkaline catalyst is added to the alcohol, or mixture thereof, or to the alkylphenol to be alkoxylated.

Catalysts which may be employed include alkali metal hydroxides, sodium ethoxide, sodium methoxide, alkali metal acetates and dimethylamine, and mixtures thereof. Preferred catalysts are the alkali metal hydroxides, more preferably sodium hydroxide and potassium hydroxide. Other types of catalysts commonly used for alkylene oxide condensation reactions may also be employed.

Optionally, a small amount of a reducing agent may be added to the alcohol, or mixture thereof, or alkylphenol to be alkoxylated to minimize discoloration of the resulting polyalkoxylated alcohol or alkylphenol. Suitable reducing agents which may be employed include sodium borohydride, lithium aluminum hydride, diborane and the like, preferably sodium borohydride.

In preparing a polyoxyalkylated alcohol or alkylphenol wherein the polyoxyalkylene chain contains a propylene oxide first block and an ethylene oxide second block, an amount of propylene oxide calculated to provide the desired degree of propoxylation is then introduced and the resulting mixture is allowed to react until the propylene oxide is consumed, as indicated by a drop in reaction pressure. A similar introduction and reaction of a calculated amount of ethylene oxide serves to provide the second block which completes the alkoxylation. Customarily, the alkoxylated product is finally treated with weak acid, e.g., glacial acetic acid, to neutralize any basic catalyst residues.

It should be understood that each separate alkoxylation procedure serves to introduce a desired average number of alkylene oxide units per alcohol or alkylphenol molecule. Thus, for example, the initial treatment of an alcohol, or mixture thereof, or alkylphenol with m moles of propylene oxide per mole of alcohol or alkylphenol serves to effect the propoxylation of each alcohol or alkylphenol moiety with propylene oxide to an average of m propylene oxide moieties per alcohol or alkylphenol moiety, although some alcohol or alkylphenol moieties will have been combined with more than m propylene oxide moieties and some will have become combined with less than m. In general, the maximum number of propyleneoxy units in a single molecule will not exceed 20 and the number of ethyleneoxy units in a single molecule will not exceed 25. The variation in the number of alkylene oxide moieties is not critical as long as the average for the number of units in each block is within the limits set out for the m and n terms in formula I above, which terms, as average values, are other than whole numbers in some instances.

Each alkoxylation is conducted at an elevated temperature and pressure. Suitable reaction temperatures are from 120° C. to about 220° C., preferably, 130° C. to 180° C. and, more preferably, 140° C. to 160° C. A suitable reaction pressure is achieved by introducing to the reaction vessel the required amount of propylene oxide or ethylene oxide, each of which has a high vapor pressure at the desired reaction temperature. The pressure serves as a measure of the degree of reaction and each alkoxylation is considered to be complete when the pressure no longer decreases with time.

For best results, it is desirable to carry out the alkoxylation under relatively moisture-free conditions and to avoid side reactions which form water. To dry the reaction vessel and connections, they may be swept out with dry, oxygen-free gas, e.g., nitrogen, before introducing the charge. The catalyst or catalyst mixture should also be dry, or substantially so. The propylene oxide and ethylene oxide should preferably be purified to remove moisture and any impurities which are capable of entering into side reactions which yield water.

The resulting alkyl or alkaryl polyalkoxide compounds are then carboxymethylated by the Williamson synthesis, involving reaction with an appropriate chloro- or bromocarboxylic acid or a salt thereof in the presence of a strong base, e.g., sodium hydroxide, sodium carbonate, etc., or by catalytic oxidation. Such reactions are ordinarily not complete; hence, the reaction products often contain minor amounts of uncarboxylated alkyl or alkaryl polyalkoxide. While methods are available for separating the uncarboxymethylated material as well as for assuring essentially complete carboxymethylation, they are usually tedious and expensive. Fortunately, it has been found that minor proportions of such uncarboxymethylated material are not particularly harmful, and may even be advantageous. The carboxymethylation involving reaction with an appropriate chloro- or bromocarboxylic acid or a salt thereof in the presence of a strong base is preferred for completeness.

The amidoamine intermediates may be prepared via a condensation reaction wherein the alkyl or alkaryl polyalkoxide carboxylic acids and an appropriate amine, e.g., 2-aminoethylethanolamine, are reacted in about equimolar proportions at elevated temperatures of between 100° C. and 220° C. and reduced pressures while removing water of condensation.

Alternatively, the amidoamine intermediates may be prepared via a condensation reaction involving the corresponding alkyl or alkaryl, polyalkoxide carboxylic acid lower alkyl esters, e.g., methyl, ethyl, isopropyl, etc., or halides, and an appropriate amine in about equimolar proportions at a temperature of between 50° C. and 150° C. For example, the amidoamine intermediates may be prepared via a condensation reaction involving the isopropyl ester of the corresponding alkyl or alkaryl, polyalkoxide carboxylic acid and an appropriate amine, with removal of isopropyl alcohol. When an alkyl or alkaryl, polyalkoxide carboxylic acid halide is used in the reaction, the reaction is conducted in a 0.45-1.10 mole ratio of carboxylic acid halide to amine, the use of an excess of amine being necessary to trap the hydrochloric acid that is formed during the reaction. Optionally, a nitrogenous base, e.g., triethylamine, pyridine, etc., may be added to the reaction mixture to trap the hydrochloric acid. If so, the reactants may be employed in about equimolar proportions The reaction of the corresponding carboxylic acid halide and an appropriate amine is usually conducted in the presence of an inert organic solvent, e.g., an aliphatic hydrocarbon such as dichloromethane, at a temperature of from 25° C. to 50° C.

The resulting amidoamine intermediates are then carboxylated by formation of an ammonium salt via a nucleophilic displacement reaction. A base need not be added due to the basicity/nucleophilicity of the amine functionality. Therefore, when an amidoamine intermediate and a chloro- or bromocarboxylic acid salt are reacted in about equimolar proportions in the presence of a common solvent, e.g., water or alcohol, at a temperature of from 25° C. to 100° C., preferably between 50° C. and 90° C., a compound of formula I where $R_2$ is hydrogen is prepared. A solvent need not be employed if the viscosity of the reaction mass allows for efficient stirring and good mass transfer.

Any further carboxylation, i.e., for preparing compounds of formula I wherein $R_2$ is —$CH_2COOM$, may be carried out by the displacement reaction described above, including the presence of a strong base to deprotonate the ammonium ion and render it nucleophilic toward the chloroor bromocarboxylic acid salt. The reaction conditions are essentially identical to that described above regarding the preparation of compounds of formula I where $R_2$ is hydrogen.

The most conspicuous property of the compounds of formula I is their great activity at surfaces and interfaces, making them especially useful as surface active agents. The uses to which surface active agents can be put are numerous and well known and, as a result, the possible applications of these new compounds are extremely varied. Thus, the surface active agents of the present invention are suitable as emusifiers, dispersing agents, detergents, wetting agents, levelling agents and the like in the textile, leather, paper, lacquer, personal care, e.g., toiletries, cosmetics, etc., and rubber industries. For instance, they can be used as wetting agents or detergents in the treating and refining of textiles; and for converting liquid or solid substances which per se are insoluble in water (such as hydrocarbons, higher alcohols, oils, fats, waxes and resins) into creamy emulsions, clear solutions or fine, stable dispersions.

In addition, the compounds of formula I are valuable emulsifiers for insecticide compositions and agricultural sprays such as DDT, 2,4-D and the like; are valuable for use as additives to petroleum products, hydraulic fluids, lubricating oils, cutting oils and greases; may be employed as coating aids for use in coating compositions comprising a hydrophilic, filmforming colloid; may be employed as tackifiers in the adhesive layer of adhesive tapes in, e.g., the photographic industry; and as foaming agents and emulsifying agents in a wide variety of food products.

The amphoteric compounds of the instant invention are especially useful as a surfactant component in shampoo compositions. Their incorporation serves to enhance not only the detergent and foaming properties of the shampoo compositions but the tactile properties as well. Such shampoo compositions will normally contain from about 5% to about 55% of an amphoteric compound of formula I, preferably from about 10% to about 45%, and more preferably from about 10% to about 40%. Although the amphoteric compounds of the instant invention may be employed as the sole surfactant thereof, i.e., totally replace the conventional anionic surfactants such as the alkyl-EO sulfates, the more preferred feature of the instant invention is to employ the amphoteric compounds of the instant invention in combination with conventional surfactants, i.e., partially replace the latter. In such shampoo compositions, the amphoteric surfactants of the instant invention will normally comprise between 20% and 50% of the weight of the mixture, preferably between 30% and 45%.

The shampoo compositions can contain other ingredients commonly found in such type compositions. For example, a fatty alkanolamide, or a mixture thereof, may be employed to assist in foam stabilization, foam boosting and in providing a cosmetically acceptable viscosity. In general, a $C_8$-$C_{18}$ mono- or dialkanolamide of the 1:1 variety (prepared by reacting equimolar amounts of the methyl ester of an appropriate carboxylic acid and a mono- or dialkanolamine) is employed. A suitable example of a monoalkanolamide is cocomonoethanolamide, and typical examples of suitable dialkanolamides are lauric diethanolamide and cocodiethanolamide.

Conditioners may also be employed and such may be quaternary ammonium compounds such as dimethyl distearyl ammonium chloride and cationic polymers such as Cartaretin F-23 (Sandoz Corporation) and Polymer JR (Union Carbide). These materials are utilized to improve the combability and manageability of damaged hair and to reduce static build-up on dry hair.

In order to improve the sheen of the hair, an oil may be present in the shampoo compositions. Such may be a silicone oil such as dimethylpolysiloxane or other conventional polysiloxanes, olive oil, or a light mineral oil.

The amount of water or aqueous vehicle to be included depends upon the desired consistency of the final product. It is possible to vary the amount of water present to formulate, for example, a thick-flowing liquid, lotion or gel. Inorganic salts such as sodium chloride can also be employed to control the viscosity.

Other conventional additives typically employed in shampoo compositions may be utilized. Fragrance oils, which mask the odor and provide cosmetic appeal, can be employed. Non-toxic and compatible dyes may be utilized to color the compositions, as desired. Preservatives, such as methyl paraben, propyl paraben and formaldehyde may be utilized.

In addition, other ingredients can be employed beneficially to provide shampoo compositions tailored to a specific use. For example, a sun screen additive such as octyl dimethyl para-aminobenzoic acid can be employed to provide hair protection. Also, products designed to provide dandruff protection can be formulated with agents such as zinc omadine (Olin).

The following examples, illustrating the novel amphoteric compounds of this invention, are presented without any intention that the invention be limited thereto.

EXAMPLE 1

N-[2-(N'-carboxymethyl-N'-(2-hydroxyethyl)ammonium)ethyl]lauryl-tetraethoxy acetamide chloride

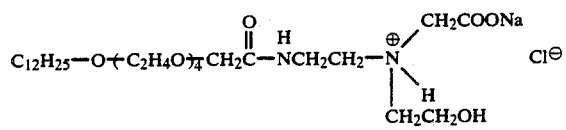

(a) Preparation of N-[2-(2-hydroxyethylamino)ethyl]-lauryl-tetraethoxyacetamide 282.6 g of lauryl-tetraethoxy acetic acid were placed in a reaction flask, heated to 70° C. under vacuum (water aspirator) to remove residual water, sparged with nitrogen and cooled to 25° C. To the reaction vessel was added, in a continuous stream with stirring under a nitrogen flow at 25° C., 52.07 g of 2-aminoethylethanolamine. The temperature of the reaction mixture gradually warmed to 49° C., over a period of 1 hour, after which time the reaction mixture was heated to 160° C. under a nitrogen flow. After 10 mls of water were collected, the heating was discontinued and the resultant product was allowed to cool to 25° C. to yield a liquid of the formula

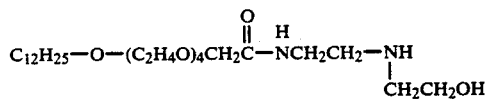

Preparation of the title compound 102.15 g of the compound prepared in a) above was dissolved in 180.3 g of distilled water and the resultant solution was placed in a reaction vessel. 17.55 g of sodium monochloroacetate was then added to the reaction vessel, with stirring. The reaction mixture was then heated to 70° C., and this temperature was maintained for 5 hours. The heating was then discontinued, which resulted in the title compound being obtained as a 40% active solution Upon cooling, the title compound was obtained as a clear yellow gel.

EXAMPLE 2

N-[2-(N',N'-bis(carboxymethyl)-N'-(2-hydroxyethyl)ammonium)ethyl]p-nonylphenoxy-nonaethoxy acetamide chloride

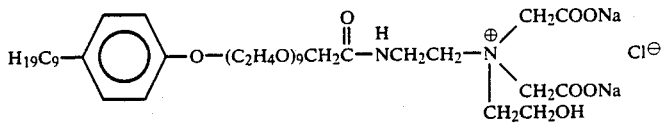

(a) Preparation of N-[2-(2-hydroxyethylamino)ethyl]p-nonylphenoxy-nonaethoxyacetamide Following essentially the procedure of Example (1a) above, and using in place of lauryl-tetraethoxy acetic acid, an approximately equivalent amount of p-nonylphenoxynonaethoxy acetic acid, a compound of the formula

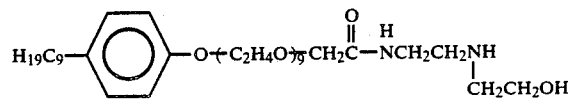

was obtained.

Preparation of the title compound 218 g of the compound prepared in (a) above was dissolved in 416 g of distilled water and the resultant solution was placed in a reaction vessel. After stirring was initiated, 30.2 g of sodium monochloroacetate was added to the reaction vessel. The reaction mixture was then heated to 75° C., and this temperature was maintained for 4 hours. The mixture was then cooled to 50° C. and 20.8 g of a sodium hydroxide solution was added. After stirring for minutes, 30.2 g of sodium monochloroacetate was added to the mixture. The resultant mixture was allowed to react overnight, while the temperature was maintained at 50° C. The heating was then discontinued, which resulted in the title compound being obtained as a light yellow, aqueous solution containing approximately 40% active.

EXAMPLE 3

N-[2-(N',N'-bis(carboxymethyl)-N'-(2-hydroxyethyl)ammonium)ethyl]isodecyl-dipropoxyhexaethoxy acetamide chloride

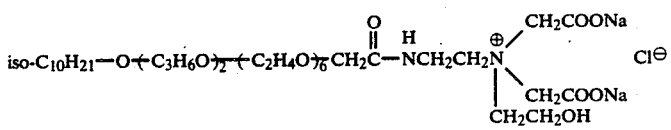

(a) Preparation of N-[2-(2-hydroxyethylamino)ethyl]isodecyl-dipropoxy-hexaethoxy acetamide Following essentially the procedure of Example (1a) above, and using in place of lauryl-tetraethoxy acetic acid, an approximately equivalent amount of isodecyl-dipropoxyhexaethoxy acetic acid, a compound of the formula

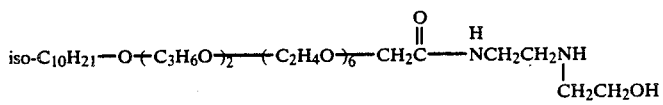

was obtained.

Preparation of the title compound

Following essentially the last step of the procedure in preparing the compound of Example 2, and using in place of the compound prepared in Example (2a), an approximately equivalent amount of the compound prepared in (a) above, the title compound was obtained as a light yellow, aqueous solution containing approximately 40% active.

EXAMPLE 4

N-[2-(N',N'-bis(carboxymethyl)-N'-(2-hydroxyethyl) ammonium)ethyl]lauryl-tetraethoxy acetamide chloride

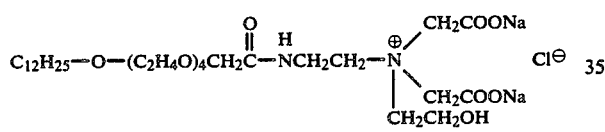

Following essentially the last step of the procedure in preparing the compound of Example 2, and using in place of the compound prepared in Example (2a), an approximately equivalent amount of the compound prepared in Example (1a), the title compound was obtained as a pale yellow, aqueous solution containing approximately 40% active.

EXAMPLE 5

To demonstrate the high degree of salt tolerance exhibited by the amphoteric compounds of the instant invention, the compound of Example 3 was tested against Miranol C2M (a commercially available amphoteric surfactant containing a coconut hydrophobe having an average chain length of 12 carbon atoms). Test samples were prepared containing 20% active surfactant and levels of sodium chloride varying from 3% to 13%. The viscosities were measured employing a Brookfield LVT viscometer at 60 rpm. As can be clearly seen from FIG. 1, the compound of Example 3 has a significantly lower viscosity at each level of salt. In addition, as the salt level increases, the viscosity response of the compound of Example 3 is less than that of Miranol C2M. Therefore, it can be concluded that the compound of Example 3 is more suitable in formulating products that contain high levels of ionic materials than is Miranol C2M. Moreover, it can additionally be concluded that the compound of Example 3 would be more effective in tertiary oil recovery where saline conditions are high than is Miranol C2M.

EXAMPLE 6

The following represent typical formulations useful as shampoo compositions.

| Ingredients | Weight Percent A | Weight Percent B |
| --- | --- | --- |
| Compound of Example 4 (on a 100% active basis) | 9.20 | 16.67 |
| Sodium Myristyl ether sulphate | 11.70 | — |
| Triethanolamine Lauryl sulphate | — | 38.90 |
| Lauric Acid diethanolamide | 3.00 | 3.30 |
| Sodium Laureth-13-Carboxylate | 0.50 | — |
| Cetyl $C_{12-15}$Pareth-9-Carboxylate | 1.00 | — |
| PEG-6000 Distearate[1] | 0.50 | — |
| Polymer JR-400[2] | — | 0.30 |
| Germaben II[3] | 1.00 | — |
| Dow 193 Surfactant[4] | 1.00 | — |
| Water | 72.10 | 40.83 |
| TOTAL | 100.00 | 100.00 |
| pH (adjusted with citric acid) | 6.5 | 6.5 |
| Total Solids (Cenco[5]) | 19.0 | 32.0 |
| Viscosity (60 rpm; spindle 4; Brookfield LVT) | 4720 cps | 4760 cps |
| Foam Height (Ross-Miles; 0.1%; mm 0/5 min.) | 172/172 | 152/150 |

[1] the reaction product of polyethylene glycol (MW = 6000) with stearic acid (2 equivalents);
[2] the reaction product of hydroxyethyl cellulose and epichlorohydrin which is subsequently quaternized with trimethylamine, available commercially from Union Carbide Corp.;
[3] a mixture of diazolidinyl urea, methyl para-aminobenzoate and propyl para-aminobenzoate in propylene glycol, available commercially from Sutton Labs, Inc.;
[4] dimethicone copolyol, available commercially from Dow Corning;
[5] type of moisture balance which utilizes an infra red lamp to remove moisture.

What is claimed is:

1. A compound of the formula I:

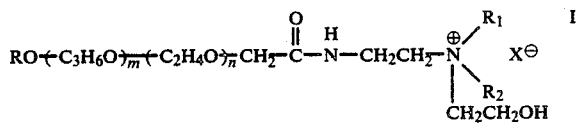

where
R is $C_6$–$C_{22}$ straight or branched chain alkyl or a group $R^1$—$C_6H_4$—, where R' is $C_6$–$C_{16}$ straight or branched chain alkyl;
$R_1$ is —$CH_2COOM$, where M is hydrogen or a cation selected from alkali metal, alkaline earth metal, ammonium, mono-, di- and tri-$C_2$–$C_4$alkanolammonium and mono-, di-, tri- and tetra- $C_1$–$C_4$alkylammonium;
$R_2$ is hydrogen or —$CH_2COOM$, where M is as defined above;
m is 0 or an integer 1 to 10;
n is an integer 2 or 15; and
$X^\ominus$ is an anion,
or a mixture of said compounds.

2. A compound according to claim 1 of formula Ia:

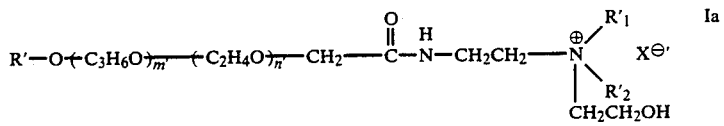

where
- R' is C$_8$–C$_{20}$ straight or branched chain alkyl or a group R$^1$—C$_6$H$_4$—, where R' is C$_6$–C$_{14}$ straight or branched chain alkyl;
- R$_1'$ is —CH$_2$COOM', where M' is hydrogen or a cation selected from alkali metal, alkaline earth metal and ammonium;
- R$_2'$ is hydrogen or —CH$_2$COOM', where M' is as defined above;
- m' is 0 or an integer 1 to 5;
- n' is an integer 2 to 12; and
- X$\ominus$' is halide, or a mixture of said compounds.

3. A compound according to claim 2 of formula Ib:

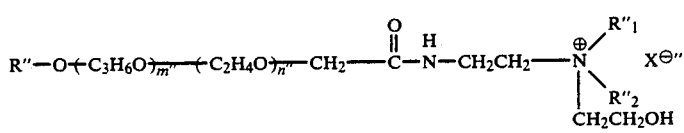

where
- R'' is C$_{10}$–C$_{20}$ straight or branched chain alkyl or a group R$^1$—C$_6$H$_4$—, where R' is C$_8$–C$_{12}$ straight or branched chain alkyl;
- R$_1''$ is —CH$_2$COOM', where M' is hydrogen or a cation selected from alkali metal and ammonium;
- R$_2''$ is hydrogen or —CH$_2$COOM', where M' is as defined above;
- m'' is 0 or an integer 1 to 3;
- n' is an integer 3 to 10; and
- X$\ominus$'' is chloride or bromide, or a mixture of said compounds.

4. A compound according to claim 3 of formula Ic:

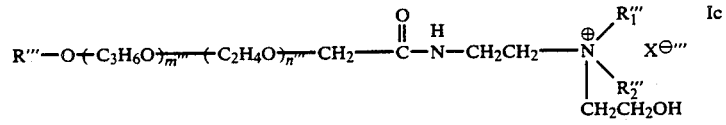

where
- R''' is C$_{12}$–C$_{18}$ straight or branched chain alkyl or a group R$^1$—C$_6$H$_4$—, where R' is C$_9$–C$_{12}$ straight or branched chain alkyl;
- R$_1'''$ is —CH$_2$COOM', where M' is hydrogen or a cation selected from sodium, potassium and ammonium;
- R$_2'''$ is hydrogen or —CH$_2$COOM', where M' is as defined above;
- m''' is 0, or an integer 1 or 2;
- n''' is an integer 4 to 9; and
- X$\ominus$''' is chloride, or a mixture of said compounds.

5. A compound according to claim 4 having the formula

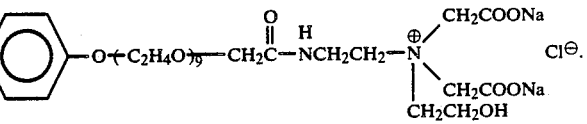

6. A compound according to claim 4 having the formula

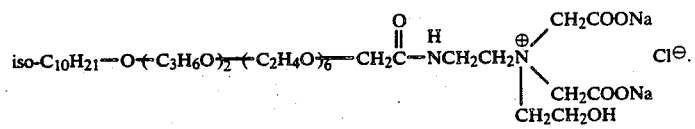

7. A compound according to claim 3 having the formula iso-C$_{10}$H$_{21}$—O(C$_3$H$_6$O)$_{\overline{2}}$(C$_2$H$_4$O)$_{\overline{6}}$—CH$_2$C—NCH$_2$CH$_2$—N(CH$_2$COONa)(CH$_2$COONa)CH$_2$CH$_2$OH Cl$\ominus$.

8. A compound according to claim 4 having the formula

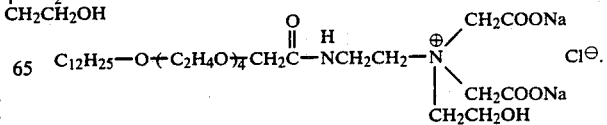

9. A shampoo composition comprising, as the essential surfactant component, from about 5% to about 55% of a compound according to claim 1, or a mixture thereof.

10. A composition according to claim 9 wherein the essential surfactant component is present in an amount of from about 10% to about 45%.

11. A composition according to claim 10 wherein the essential surfactant component is present in an amount of from about 10% to about 40%.

12. A shampoo composition comprising, as the sufactant component, a mixture of an anionic surfactant and a compound of formula I according to claim 1, the latter being present in an amount of from about 20% to about 50% of the weight of the mixture.

13. A composition according to claim 12 wherein the compound of formula I is present in an amount of from about to about 45% of the weight of the mixture.

* * * * *